(12) United States Patent
Edouard et al.

(10) Patent No.: US 11,937,923 B2
(45) Date of Patent: Mar. 26, 2024

(54) NON-INVASIVE METHOD TO DETERMINE BLOOD OXYGEN SATURATION LEVEL

(71) Applicant: WITHINGS, Issy les Moulineaux (FR)

(72) Inventors: Paul Edouard, Issy les Moulineaux (FR); Romain Kirszenblat, Issy les Moulineaux (FR)

(73) Assignee: WITHINGS, Issy les Moulineaux (FR)

( * ) Notice: Subject to any disclaimer, the term of this patent is extended or adjusted under 35 U.S.C. 154(b) by 462 days.

(21) Appl. No.: 17/245,139

(22) Filed: Apr. 30, 2021

(65) Prior Publication Data

US 2021/0338118 A1    Nov. 4, 2021

(30) Foreign Application Priority Data

Apr. 30, 2020    (EP) ................................. 20305419

(51) Int. Cl.
*A61B 5/1455*    (2006.01)
*A61B 5/00*    (2006.01)

(52) U.S. Cl.
CPC ........ *A61B 5/14551* (2013.01); *A61B 5/0004* (2013.01); *A61B 5/681* (2013.01); *A61B 5/7225* (2013.01); *A61B 5/7264* (2013.01); *A61B 5/721* (2013.01)

(58) Field of Classification Search
CPC ... A61B 5/14551; A61B 5/0004; A61B 5/681; A61B 5/7225; A61B 5/7264; A61B 5/721; A61B 5/7221; A61B 5/742
See application file for complete search history.

(56) References Cited

U.S. PATENT DOCUMENTS 6,615,061 B1 *    9/2003    Khalil ................ A61B 5/14532
                                                        600/316
10,874,348 B1 *   12/2020    Han ..................... A61B 5/6843
(Continued)

FOREIGN PATENT DOCUMENTS

EP          3238615 A1      11/2017
WO       2016199124 A1      12/2016

OTHER PUBLICATIONS

European Search Report related to U.S. Appl. No. 20/305,419 reported on Aug. 17, 2020.
(Continued)

*Primary Examiner* — Eric F Winakur
*Assistant Examiner* — Abid A Mustansir
(74) *Attorney, Agent, or Firm* — Pillsbury Winthrop Shaw Pittman LLP (57) ABSTRACT

A non-invasive method to determine a current functional blood oxygen saturation level: acquiring, at a sampling frequency, a photoplethysmography light response for each wavelength of a plurality of at least three wavelengths, resulting respectively in a first, second and third raw data series, applying a low-pass filter to each of the first, second and third raw data series, resulting respectively in a first, second and third DC data series representing an unmodulated amplitude response determining respectively in a first, second and third AC data series representing an unmodulated amplitude response, applying a. computation engine to the first, second and third AC and DC data series, and determining therefrom a user current blood oxygen saturation level.

24 Claims, 8 Drawing Sheets

(56) References Cited

U.S. PATENT DOCUMENTS

| | | | |
|---|---|---|---|
| 2004/0034294 A1* | 2/2004 | Kimball | A61B 5/6826 600/323 |
| 2007/0049810 A1 | 3/2007 | Mannheimer et al. | |
| 2009/0287070 A1* | 11/2009 | Baker, Jr. | G16Z 99/00 600/324 |
| 2010/0049018 A1* | 2/2010 | Duffy | A61B 5/14552 600/323 |
| 2010/0087720 A1* | 4/2010 | Addison | A61B 5/14551 600/345 |
| 2012/0209095 A1* | 8/2012 | Huiku | A61B 5/14551 600/322 |
| 2014/0275850 A1* | 9/2014 | Venkatraman | A61B 5/02427 600/595 |
| 2016/0302674 A1* | 10/2016 | Moyer | A61B 5/259 |
| 2017/0296104 A1 | 10/2017 | Ryan | |
| 2018/0301224 A1 | 10/2018 | Matichuk et al. | |
| 2018/0317785 A1 | 11/2018 | MacDonald | |
| 2019/0083034 A1 | 3/2019 | Shim et al. | |
| 2019/0223791 A1 | 7/2019 | Sayani et al. | |
| 2019/0246967 A1 | 8/2019 | Pekander et al. | |
| 2020/0000441 A1 | 1/2020 | Lafon et al. | |

OTHER PUBLICATIONS

Ding Xinyi et al: "Measuring Oxygen Saturation with Smartphone Cameras Using Convolutional Neural Networks", IEEE Journal of Biomedical and Health Informatics, IEEE, Piscataway, NJ, USA, vol. 23, No. 6, Nov. 6, 2019 (Nov. 6, 2019), pp. 2603-2610, XP011754103, ISSN: 2168-2194, D0I: 10.1109/JBHI.2018. 2887209 [retrieved on Nov. 7, 2019] *abstract; p. 2603, col. 1-col. 2* p. 2606, col. 1 *p. 2608, col. 2* p. 2609, col. 2*.

Cheng-Chun Chang et al: "NW-PPG Sensor: An on Chip Spectrometer Approach", Sensors, vol. 19, No. 17, Aug. 26, 2019 (Aug. 26, 2019), p. 3698, XP055657845, D0I: 10.3390/s19173698 *figures 1, 2, 6*.

* cited by examiner

NON-INVASIVE METHOD TO DETERMINE BLOOD OXYGEN SATURATION LEVEL

TECHNICAL FIELD

This disclosure pertains to the field of devices allowing to measure a functional blood oxygen saturation level (SpO2) of an individual. More precisely, this disclosure is directed to a pulse oximetry method, for measuring a functional blood oxygen saturation level. The measuring site can be notably but non exclusively a wrist of an individual.

BACKGROUND ART

A technique for monitoring certain physiological parameters of a patient is commonly referred to as "pulse oximetry", and the devices built based upon pulse oximetry techniques are commonly referred to as pulse oximeters. Pulse oximetry may be used to measure various blood characteristics, such as the arterial blood oxygen saturation of hemoglobin (SaO2/SpO2). In practice SpO2 is usually referred as "Peripheral Oxygen Saturation", used as a proxy to replace an invasive measurement of arterial blood oxygen saturation (SaO2).

However, it is important that "Peripheral Oxygen Saturation" SpO2 gives a faithful and reliable image of the arterial blood oxygen saturation (SaO2), especially if the measuring device qualifies as a medical grade device. For a medical grade device, maximum deviation of SpO2 versus SaO2 is defined by ISO 80601-2-61:2017 standard.

Pulse oximetry techniques typically utilize a tissue site that is well perfused with blood, such as a patient's finger, to place the sensor thereto.

But having a clip like sensor at a finger strongly impedes the user from having a normal activity. And in addition, often such sensor location requires the patient (or user) to be confined to a certain area, in close vicinity of an associated monitoring system, thereby limiting patient mobility.

There remains a need to provide an oximeter-enabled device that can be really worn as a non-invasive, user-friendly device, which complies with the accuracy requirements of ISO 80601-2-61.

The inventors have sought to propose methods and devices suitable for accurate pulse oximetry at various measuring anatomical sites, like for example and non exclusively: wrist, forehead, earlobe, ear-canal, ankle, sole, arm.

SUMMARY OF THE DISCLOSURE

To this aim, it is promoted herein a method to determine a current functional blood oxygen saturation level (SpO2), the method comprising:
a—acquiring, at a predefined sampling frequency, a photoplethysmography light response for each wavelength of a plurality of at least three wavelengths ($\lambda 1$, $\lambda 2$, $\lambda 3$), resulting respectively in a first, second and third raw data series representing an amplitude response through a user's tissue,
b—applying a low-pass filter to each of the first, second and third raw data series, resulting respectively in a first, second and third DC data series representing an unmodulated amplitude response
c—applying a high-pass filter (c1) to each of the first, second and third raw data series, or (c2—) subtracting respectively first, second and third DC data series to said first, second and third raw data series, to result respectively in a first, second and third AC data series representing an unmodulated amplitude response,
d—applying a computation engine to the first, second and third AC data series, and to the first, second and third DC data series, and determining therefrom a user current blood oxygen saturation level (SpO2).

Thanks to this arrangement, the use of three wavelengths PPG response allows a reliable and accurate assessment a user current blood oxygen saturation level.

The computation engine can be of a neural network type or can be a rule-based type algorithm. The above digital filters and the computation engine are used in a subsequent manner. The above digital filters and computation engine only require little memory and computation power.

The following features, can be optionally implemented, separately or in combination one with the others.

According to one option, the computation engine comprises a one dimension convolutional Neural Network (1DCNN). We use an optimized Neural Network requiring a limited amount of resources, in terms of memory and computing power.

According to another option, the computation engine comprises a LSTM Neural Network, i.e. a Long Short Term Memory Neural Network. We may use recurrence provided in LSTM neural network to get another optimal solution for the computation engine.

According to one option, step d— begins by:
computing a first ratio ($AC1i/DC1i$), namely the latest element of the first AC data series divided by the latest element of first DC data series, giving a first ratio data series (AC1/DC1),
computing a second ratio ($AC2i/DC2i$), namely the latest element of the second AC data series divided by the latest element of second DC data series, giving a second ratio data series (AC2/DC2),
computing a third ratio ($AC3i/DC3i$), namely the latest element of the third AC data series divided by the latest element of third DC data series, giving a third ratio data series (AC3/DC3),
and the computation engine computes said first, second and third ratio data series. AC/DC ratios prove to be the most relevant data to work with in an optimized way.

According to one option, the one dimension convolutional Neural Network (1DCNN) may comprise an input layer fed only by first, second and third ratio data series. Thereby we use a CNN with a limited and reasonable number of dimensions and it can be embedded in a cost effective computation unit.

According to one option, the one dimension convolutional Neural Network exhibits less than 1000 weight coefficients, and exhibits less than 1500 floating point multiplications per second. Such CNN requiring a limited amount of resources, in terms of memory and computing power can be embedded in a low cost computation unit.

According to one option, the plurality of at least three wavelengths ($\lambda 1$, $\lambda 2$, $\lambda 3$) comprises:
a first wavelength ($\lambda 1$) which has a center emission wavelength comprised between at 920 nm and 960 nm and forms an infrared LED,
a second wavelength ($\lambda 2$) which has a center emission wavelength comprised between at 650 nm and 665 nm and forms a red LED,
a third wavelength ($\lambda 3$) which has a center emission wavelength comprised between 480 nm and 540 nm and forms a green or blue LED.

We therefore use substantial differences regarding hemoglobin, notably deoxygenated and oxygenated hemoglobin absorption indices between infrared and red wavelengths, and besides we use the strong pulsatile signal given by the green wavelength.

According to one option, the method may further comprise one or more of:
- displaying the so determined current blood oxygen saturation level on a display intended to be looked at by a user
- providing the so determined current blood oxygen saturation level to a remote entity, preferably via a wireless transmission.

Results are therefore displayed directly to the user/wearer and can be forwarded to another device either belonging to the user or to some medical staff/caretaker.

According to one option, the light responses for each wavelength are taken at a user's wrist.

This turns to be a practical location for permanent wear, and also a user-friendly location.

According to one option, steps a— to d— are implemented in a control unit housed in a wrist-worn device. A stand-alone unit can perform all the process of the promoted method.

According to one option, the wrist-worn device is a wristwatch. Further, the device can give current time; further such the device is good looking and does not look like a medical device although it can give a medical grade SpO2 information.

According to one option, the whole method is carried out repeatedly on a user or a patient, wherein steps a— to d—, once executed, are repeated after a predefined wait time comprised between 5 minutes and 30 minutes.

It is this possible to continuously monitor of a user/patient, whereas simultaneously optimizing usage of electrical energy. An alert can be given/transmitted to a caretaker in case the SPO2 drops significantly across some subsequent measurements.

According to one option, the device may comprise a motion sensor, and whenever a motion greater than a predetermined threshold is sensed, the method further comprise a momentary suspension of displaying and outputting of the user current blood oxygen saturation level. Since the measurement is disturbed by a movement of the site (wrist or else), it is preferable not to output an inaccurate result. Motion sensor signals can also be used to notify the user/patient that he/she should stay still for a short while since a measurement is on-going.

According to one option, the method may further comprise a worn test function, wherein whenever the worn test function gives a negative result, at least displaying and outputting of the user current blood oxygen saturation level are suspended, and possibly the computation is also suspended. It is useless to display a result with no significance whenever the device is not worn on user's tissue. Further, electrical energy can be spared whenever the device is not worn According to one option, the predefined sampling frequency (SF) is comprised between 15 Hz and 200 Hz, preferably comprised between 15 Hz and 50 Hz, more preferably comprised between 20 Hz and 30 Hz. This is a good compromise regarding accuracy and electrical energy consumption According to one option, at the step a—, the acquisition of PPG photoplethysmography light response is performed by two photodiodes, i.e. a broadband photodiode (2) configured to receive red and infrared light rays, and a selective photodiode (3) configured to receive green light rays. This results in an optimization of photodiode usage, selective photodiode is dedicated to green wavelength, sensitivity of broadband photodiode is interesting for red and infrared wavelengths.

According to one option, steps b— to d— are performed each time a new set of wavelength light responses is acquired, namely all process is timely triggered according to the predefined sampling frequency clock.

Thereby a simple task handling within the control unit is sufficient. Optimal electrical energy consumption is also achieved.

The present disclosure also promotes a device comprising a plurality of LEDs (11,12,13) configured to emit light rays at three or more wavelengths ($\lambda 1, \lambda 2, \lambda 3$), and at least a light sensing device, a control unit, the device being formed as a single unit and configured to carry out a method as proposed above. It should be understood that each of the optional features stated above can be carried out in such integral device.

BRIEF DESCRIPTION OF DRAWINGS

Other features, details and advantages will be shown in the following detailed description and on the figures, on which.

DESCRIPTION OF EMBODIMENTS

Overall and PPG Basics

As shown on figures, an oximeter wristwatch 9 is provided. As will be exposed below, the wristwatch exhibits an oximeter function, namely an assessment of a current functional blood oxygen saturation level (SpO2).

We note also that the wristwatch can also exhibit an ECG function (i.e. Electro Cardio Gram).

However, the wristwatch is only one example among other devices for measuring one or more bio-parameter(s) to assess a current functional blood oxygen saturation level (SpO2).

Other anatomical site(s) different from the wrist is also considered. Other types of device(s) besides wristwatch or wristband are also considered. A non-limiting list can be: forehead, earlobe, ear-canal, ankle, sole, arm, etc.

The measuring device can applied momentarily, on the long run or permanently to the anatomical site(s).

We use a technique termed photoplethysmography or, in short, "PPG" for obtaining the above one or more physiological parameters reflecting blood circulation in the tissue of the anatomical site(s)).

PPG involves a non-invasive optical sensor that detects the light response from within a patient's tissue indicative of the amount of light absorbed within the tissue at the illuminated site.

As will now be seen below, we use several wavelengths.

Turning back to the wristwatch illustrated example, there is provided a main casing 90 and a wristband 19 attached thereto. Further there is provided, attached to the main casing 90 of the wristwatch, a back-case assembly generally denoted 8. The back-case assembly 8 comprises, from the center, going radially outwards: a lens 4, a ring member 81 and an annular cup member 82.

The lens 4 forms a transparent or translucent window allowing optical interaction between the wristwatch and the environment at its back; notably the wrist skin WS.

For an analog display watch like the one illustrated, we note that there is provided a front dial with a circular shape, and the backside lens is also circular, i.e. the lens is a transparent disk. However we note that the wristwatch can have a different overall shape like a rounded rectangle, a rounded square, an oval shape.

Behind the lens 4, there is provided a light emission assembly 1. The light emission assembly 1 comprises a green LED 13, a red LED 12 and an infrared LED 11. LED stands for Light Emission Diode.

In the present disclosure, the infrared LED 11 has a center emission wavelength comprised between 920 nm and 960 nm. According to one particular example, the infrared LED 11 has a center emission wavelength at 940 nm.

More generally speaking, we use a first wavelength denoted $\lambda 1$, in the infrared wavelength part of the spectrum.

In the present disclosure, the red LED 12 has a center emission wavelength comprised between 650 nm and 665 nm. According to one particular example, the red LED 12 has a center emission wavelength at 655 nm.

More generally speaking, we use a second wavelength denoted $\lambda 2$, in the red wavelength spectrum.

In the present disclosure, the green LED 13 has a center emission wavelength comprised between 480 nm and 540 nm. According to one particular example, the green LED 13 has a center emission wavelength at 530 nm.

It is to be understood in the present disclosure that "green" has been given a broad scope, also encompassing partly of the blue wavelengths, at least the blue/green nuances.

More generally speaking, we use a third wavelength denoted $\lambda 3$, in the green/blue wavelength spectrum.

Figure 7:
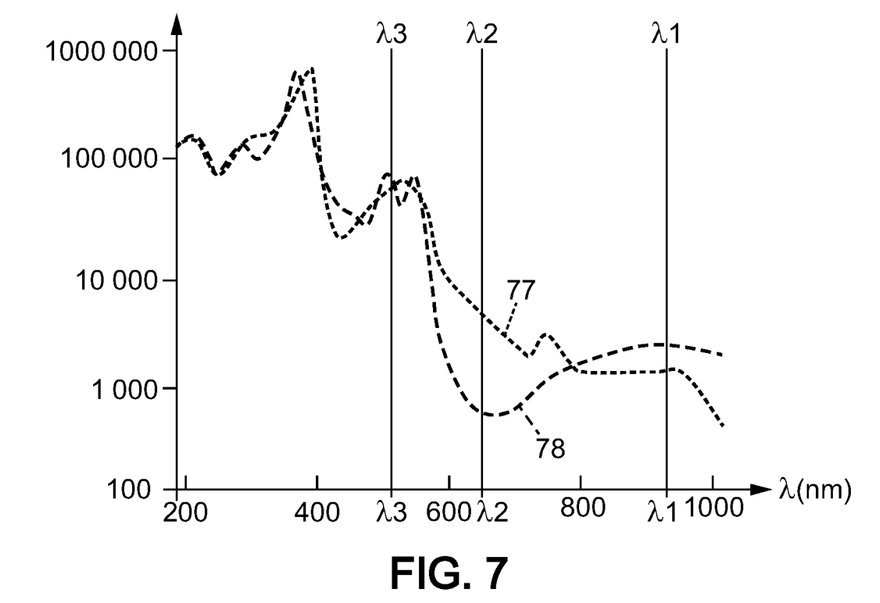
FIG. 7 shows an absorption chart relating to Hemoglobin.

As apparent from FIG. 7, we note that the three wavelengths $\lambda 1$, $\lambda 2$, $\lambda 3$ are spread/distributed across the light spectrum (visible+infrared).

On FIG. 7, curve 77 denotes the absorption index of deoxygenated Hemoglobin, whereas curve 78 denotes the absorption index of oxygenated Hemoglobin. The difference between the 2 curves influences the PPG responses.

Figure 4:
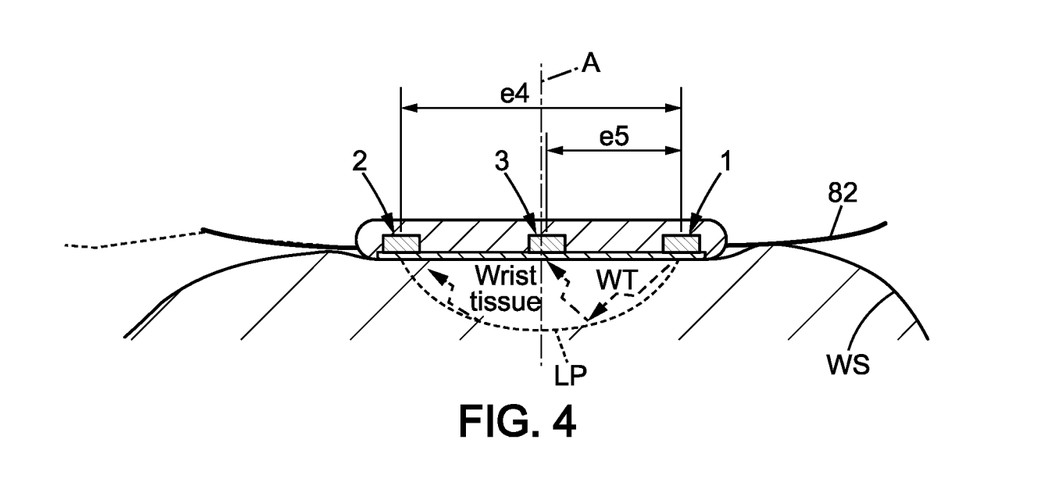
FIG. 4 shows more in details an elevation sectional of the wristwatch back case bearing on the wrist skin.

Each LED is configured to emit light rays toward wrist tissue WT through the lens 4, and some light is perfused through the site tissue. There is provided at least a broadband photodiode 2 configured to receive light rays. From the LED, there is defined a Light Path denoted LP from the LED to the broadband photodiode (cf. FIG. 4). Only one photodiode can be used to receive the three wavelengths light rays.

In the shown example, the acquisition of PPG photoplethysmography light response is performed by two photodiodes, i.e. a broadband photodiode 2 configured to receive red and infrared light rays, and a selective photodiode 3 configured to receive green light rays.

The light intensity received at the photodiode is converted into a digital value by a ADC 16 (Analog to Digital Converter), so it can be readily handled by computation means.

For an optimization of photodiodes usage, selective photodiode is dedicated to green wavelength, sensitivity of broadband photodiode is interesting for red and infrared wavelengths.

Figure 10:
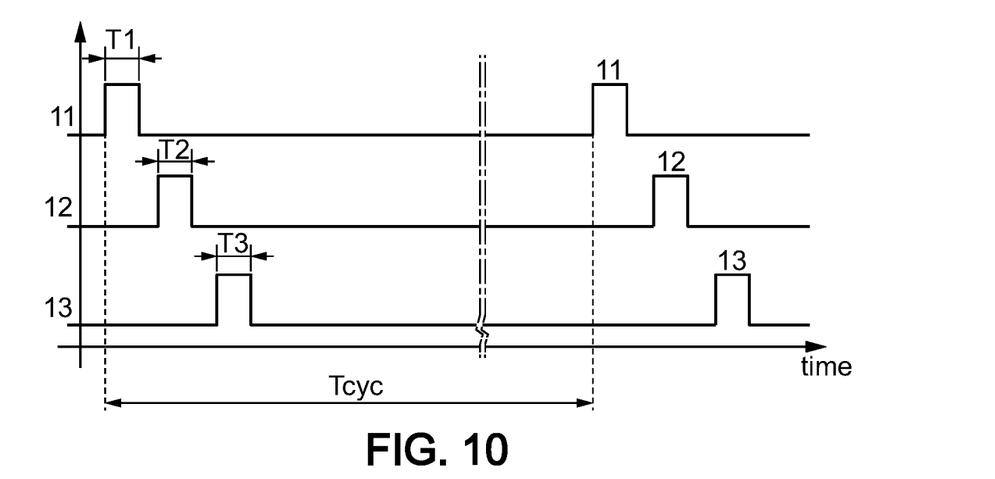
FIG. 10 shows a time chart illustrating the selective activation of the various wavelengths LEDs.

As shown at FIG. 10, each LED is selectively activated, one after another. Wavelengths are timely segregated and optical crosstalk is reduced. For one measure, each LED is activated for a short time. According to the illustrated example, first the infrared LED is activated for a duration T1, comprised between 50 microseconds and 200 microseconds. Then the red LED is activated for a duration T2, comprised between 50 microseconds and 200 microseconds. Then the green LED is activated for a duration T3, comprised between 50 microseconds and 200 microseconds. LED activation phases are separated by a pause time that can be for example comprised between 10 microseconds and 50 microseconds.

After the three LED activation phases, calculation steps take place as will be discussed later.

Sampling overall process is repeated with a sequence duration Tcyc. Tcyc corresponds to sampling frequency SF (i.e. 1/Tcyc). The sampling frequency SF is comprised between 15 Hz and 200 Hz, preferably comprised between 15 Hz and 50 Hz, more preferably comprised between 20 Hz and 30 Hz.

In the illustrated example, the sampling frequency SF is 25 Hz, which is a good compromise regarding accuracy and electrical energy consumption. Tcyc is 40 milliseconds in this example.

Higher sampling frequencies are also possible, namely above 40 Hz up to hundreds of Hz.

It is to be noted that the current flowing in each LED when each LED can be interestingly selectively adaptively controlled. The PPG function can be readily adapted to the skin nature and color/tone of a large scope of users.

Sampling and Computation

As time passes, the sampling process collects periodically three light response values. As illustrated on FIG. 8, we illustrate the process about one of the wavelength data series. For the two other wavelengths, there are likewise similar curves and process.

Figure 5:
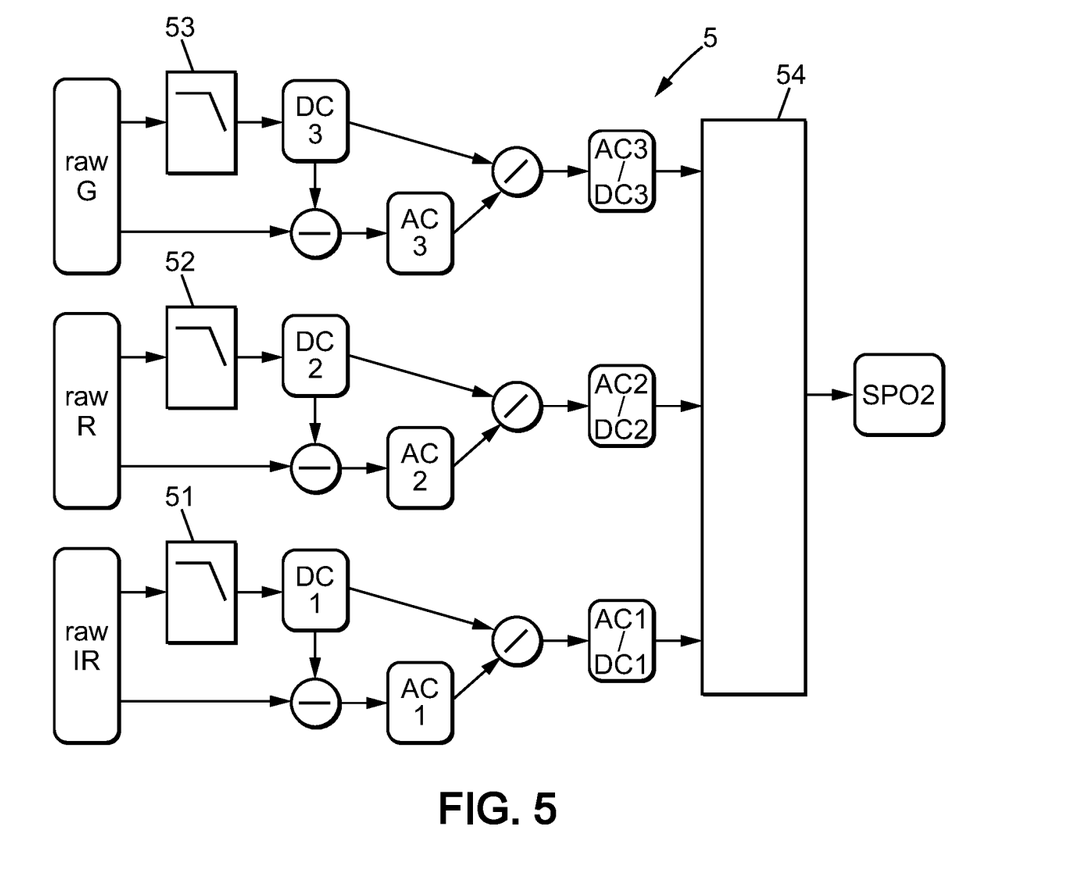
FIG. 5 shows a functional block diagram.
Figure 6:
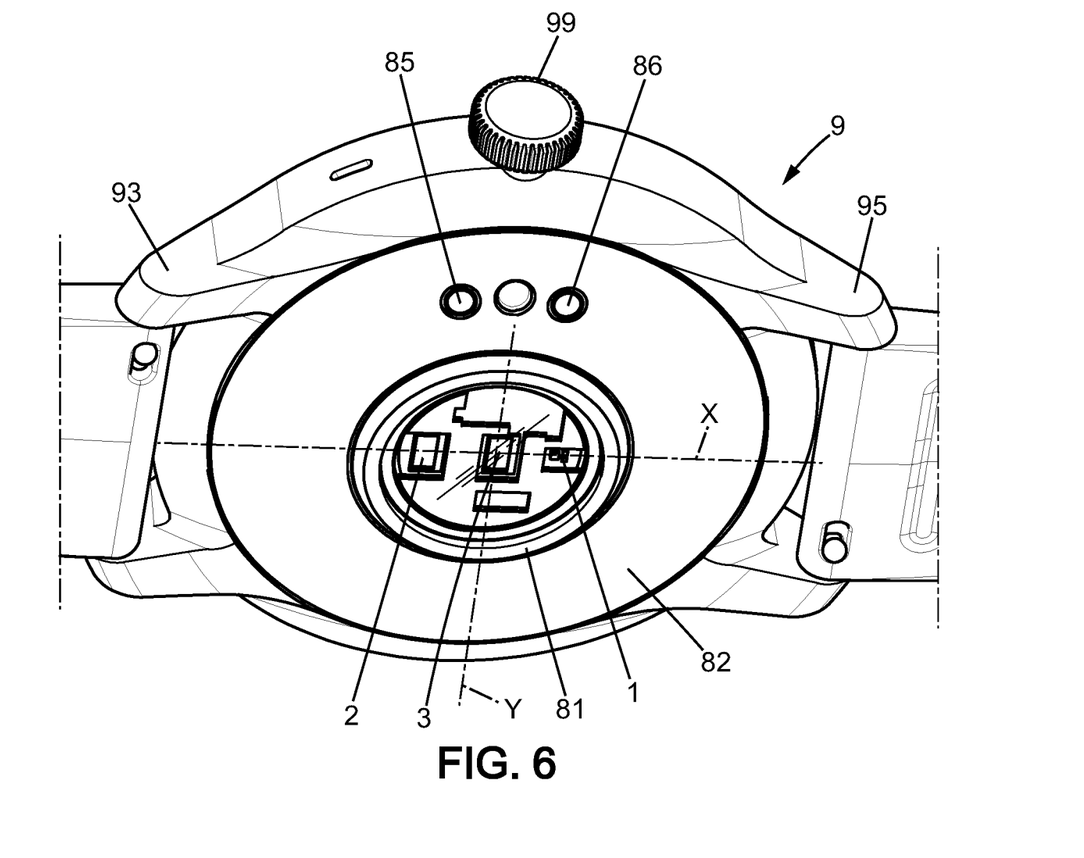
FIG. 6 shows a bottom perspective view of the oximeter wristwatch of FIG. 1.
Figure 8:
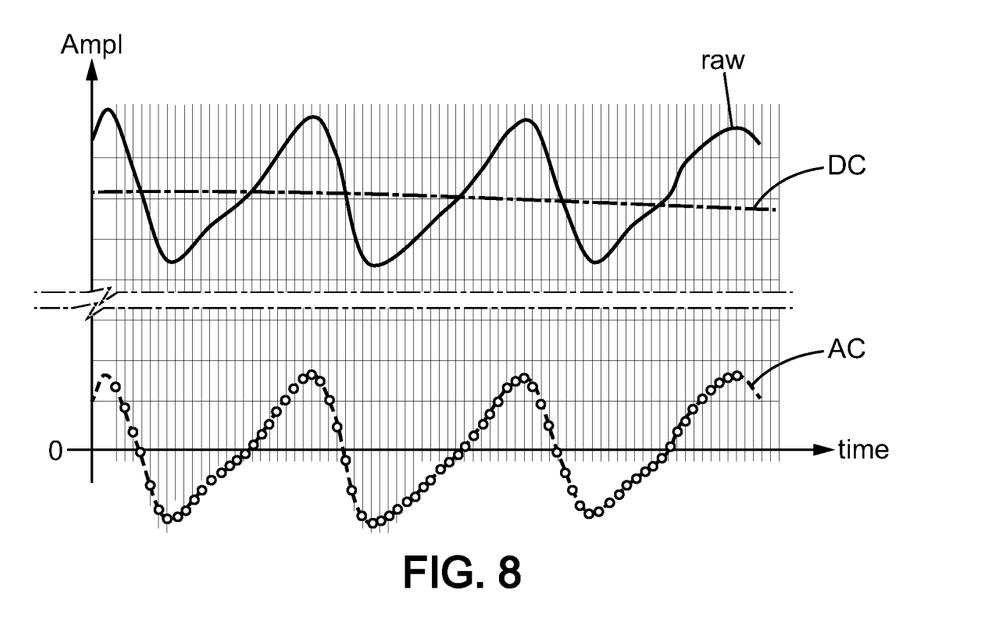
FIG. 8 shows one of the wavelength data series, raw, DC and AC.

The collected data is named raw data, and is shown by bold line at the top area of FIG. 8 ('raw'). As shown at FIG. 5, the raw data series are respectively denoted rawG for the green wavelength, rawR for the red wavelength rawIR for the infrared wavelength.

The raw data series is to be decomposed in a DC data series and AC data series. DC stands for 'continuous' or 'unmodulated' component, whereas AC stands for 'alternative' or 'modulated' or 'pulsatile' component.

In one embodiment, at a step denoted b—of the promoted method, a low-pass filter is applied to the raw data series to give a resulting DC data series representing an unmodulated amplitude response.

The low-pass filter can have a cutoff frequency of 6 Hz. Practically the low-pass filter can have a cutoff frequency comprised between 3 Hz and 8 Hz. A rather simple finite impulse response digital filter can be used here.

As apparent from FIG. 5, there are provided a first low-pass filter 51 which gives as output a first DC data series DC1, a second low-pass filter 52 which gives as output a second DC data series DC2 a third low-pass filter 53 which gives as output a third DC data series DC3.

On the other hand, the AC component is also to be extracted from each raw data series, at a step denoted c— of the promoted method.

According to one possibility, as shown as FIG. 5, for each wavelength series, the DC data series is subtracted from the raw data series to give a resulting AC data series representing a modulated amplitude response. More precisely, we obtain here a first AC data series AC1, a second AC data series AC2 and a third AC data series AC3.

Figure 11:
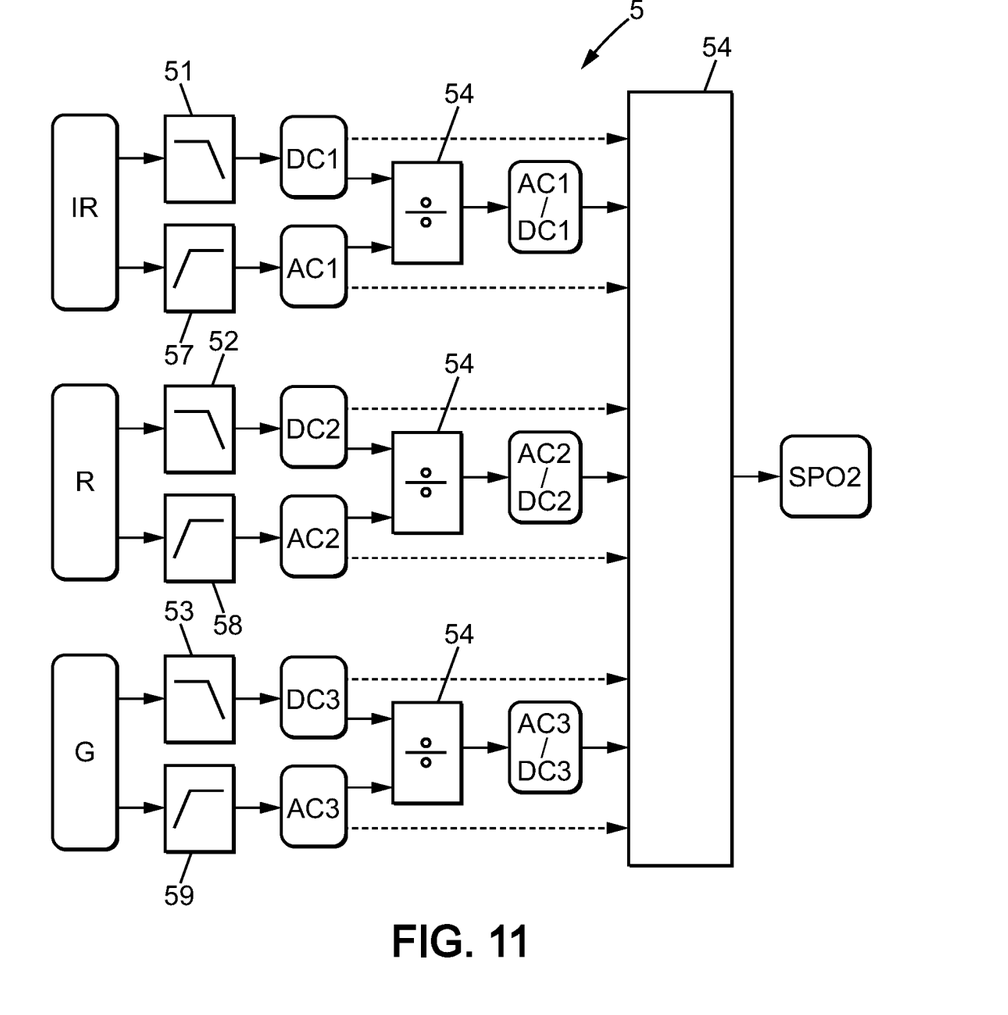
FIG. 11 shows a variant of functional block diagram.

According to another possibility, as shown as FIG. 11, a high-pass filter is applied directly to the raw data series each to give a resulting AC data series representing a modulated amplitude response.

Further, there is provided a control unit 6 housed in a wristwatch or in any other device like a hearing aid, a necklace, an activity tracker, a body scale, a blood pressure monitor device, a forehead thermometer device, a forehead band, etc. . . . .

In many embodiments of such devices, we note that the promoted method is performed within a device formed as an integral device, i.e. a single unit. Such unit houses herein said control unit 6, LEDs, light and motion sensors, and possibly a battery. It can be autonomous for measuring SpO2, without requiring external further sensor.

The control unit 6 is configured to control the LEDs, receive response signal at photodiode(s) and perform various computation steps.

More precisely, the control unit 6 is configured to collect electrical signals delivered by the selective and broadband photodiodes (2, 3) upon selective activation of each LED of the light emission assembly 1. The control unit 6 is configured to calculate therefrom a current blood oxygenation level (SpO2).

Further, the wristwatch comprises a motion sensor 15. The motion sensor can include linear accelerometer device for local Cartesian sensing along axis X,Y,A. The motion sensor can include gyro-meter sensing ωX, ωY, ωA. The motion sensor can include both a linear accelerometer device and a gyrometer sensing device, or only one of them.

Further, the wristwatch comprises a wireless coupler 117, such that collected and/or computed data can be forwarded to a server 67. Further, the wristwatch may comprise one or more night reading illumination light source 62.

At step d— of the promoted method the control unit 6 is configured to apply a computation engine 5 to the first, second and third AC data series (AC1, AC2, AC3), and to the first, second and third DC data series (DC1, DC2, DC3). The control unit 6 is configured to determine therefrom a user current blood oxygen saturation level SpO2.

Figure 12:
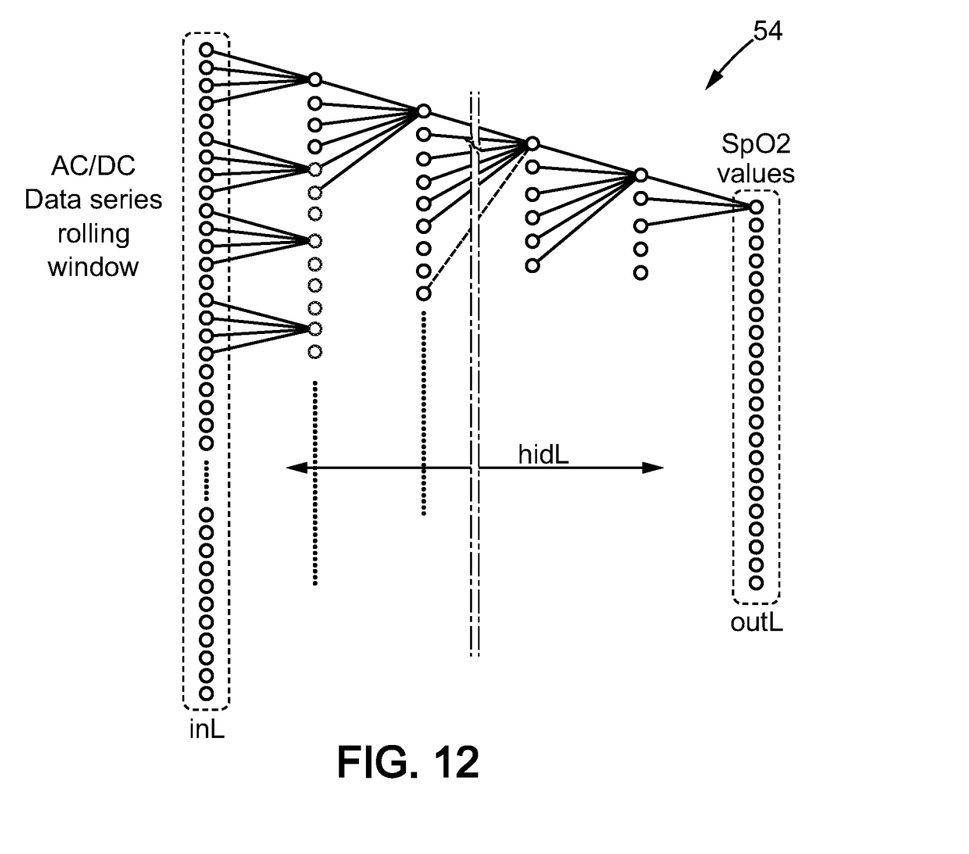
FIG. 12 shows a functional illustration of a one dimension convolutional Neural Network.

Among various possibilities to embody such computation engine, it is promoted herein a one dimension convolutional Neural Network 54, termed in short 1DCNN.

However, it should be noted that the computation engine can be embodied in a conventional full layer Neural Network, or even in a conventionally programmed rules.

The latest acquired light responses, converted into digital values are denoted as follows, where the index i is the latest acquisition index:

rawIR (i) is the latest acquired element at the first wavelength λ1,
rawR (i) is the latest acquired element at the second wavelength λ2,
rawG (i) is the latest acquired element at the third wavelength λ3, AC1$i$ denotes the latest element of the first AC data series,
DC1$i$ denotes the latest element of the first DC data series,
AC2$i$ denotes the latest element of the second AC data series,
DC2$i$ denotes the latest element of the second DC data series,
AC3$i$ denotes the latest element of the third AC data series,
DC3$i$ denotes the latest element of the third DC data series.

A first ratio is computed (AC1$i$/DC1$i$), which is the latest element of the first AC data series divided by the latest element of first DC data series.

A second ratio is computed (AC2$i$/DC2$i$), which is the latest element of the second AC data series divided by the latest element of second DC data series.

A third ratio is computed (AC3$i$/DC3$i$), which is the latest element of the third AC data series divided by the latest element of third DC data series.

The subsequent results of the first ratio computations gives a first ratio data series (AC1/DC1). The subsequent results of the second ratio computations gives a second ratio data series (AC2/DC2). The subsequent results of the third ratio computations gives a third ratio data series (AC3/DC3).

The 1D Convolutional Neural Network (1DCNN) comprises an input layer inL fed only by first, second and third ratio data series, namely (AC1/DC1, AC2/DC2, AC3/DC3).

More precisely, as shown at FIG. 12, the AC/DC data series are injected into the input layer as a rolling window of the more recent calculation. The depth/width of the window can be as large as 100 for each channel (e.g. from i-99 to i) namely this means about 300 points/neurons at the input layer.

According to another option, the depth/width of the window can be as large as 250 for each channel (e.g. from i-249 to i) namely this means about 750 points/neurons at the input layer.

According to another option, the depth/width of the window can represent a certain time of sampling, said certain time can be comprised between 2 seconds and 20 seconds, for instance around 10 seconds.

The number of hidden layers can range from 2 to 10 or more. Some of the hidden layers can be pooling layers.

Not only the first hidden layer can be a 1D convolutional Neural Network, there may be provided an additional 1D convolutional Neural Network in one further hidden layer, i.e. several convolutional layers can be provided in the Neural Network.

In the example promoted here, the 1D Convolutional Neural Network has for the convolution function a 'width' of 3 to 20 neuron links.

According to one option, the output layer outL may comprise a set of discrete SpO2 values ranging from 65% to 100%, with 0.5 as increment, i.e. about 70 output neurons. According to another option, the output layer comprises a set of discrete values ranging from 65% to 100%, with 0.2 as increment, i.e. about 175 output neurons.

Alternately, According to another option, the output layer outL may comprise a single neuron, the value of which is the outputted SpO2.

According to particular embodiment, the 1D convolutional Neural Network 54 exhibits less than 1000 weight coefficients, and exhibits less than 1500 floating point multiplications per second.

As known per se, a deep learning process, intended to tweak the various weights involved, is also to be carried out.

This can be done partly, with a set of patients for some of which a parallel SaO2 invasive measure is carried out. This can be done also with patients having on the one hand a fingertip SpO2 sensing system, and on the other hand the device under deep learning process.

Besides, alternatives to the 1D convolutional Neural Network are considered in the present disclosure. 2D convolutional Neural Network can be carried out, "2D" standing for two dimensional. Also the computation engine can comprise a LSTM Neural Network, i.e. a Long Short Term Memory Neural Network. We may use recurrence of LSTM neural network to provide another optimal solution for the computation engine. Other recurrent Neural Network topologies are not excluded. Fully connected topologies are also considered.

According to one option, the device (wristwatch or other) comprises the already mentioned motion sensor 15, which influences the calculation and/or the output process.

For example, whenever a motion greater than a predetermined threshold is sensed, the method further comprising a momentary suspension of displaying and outputting of the user current blood oxygen saturation level. Advantageously, when the measurement is disturbed by a movement of the site (wrist or else), it is preferable not to output an inaccurate result.

According to one option, the device (wristwatch or other) comprises a worn test function. The worn condition can be determined by comparing the light response with a range of possible light response expected when the device is applied to a human tissue.

According to one option, the worn test function relies on the infrared LED. Namely, when the worn test is assumed to be false, a new worn test is carried out periodically, for example every 5 minutes or 30 minutes, by activating the infrared LED and checking the IR light response. The period of checking can be made dependent on the motion signals delivered by the motion sensor.

Also, the worn test function can be related to the blood oxygen saturation level (SpO2) function, or alternatively, the worn test function can be unrelated to the SpO2 function if another function of the watch requires the worn condition to be updated more often.

For example, if the motion signals are null or below a small threshold, the worn checking test can be slowed down to one every 10 minutes. And conversely, when motion signals are greater, the worn test can be made more frequently.

According to one embodiment, the worn test is performed every time SpO2 a measurement is needed, just before the SpO2 measurement cycle. If motion signals are two large, it can be decided to postpone the SpO2 measurement cycle until the motion signals are small enough, or it can be decide to repeat the SpO2 measurement cycle until the motion signals are small enough.

When the worn test function gives a negative result, displaying and outputting of the user current blood oxygen saturation level are suspended, and possibly the computation is also suspended. It is useless to display a result with no significance whenever the device is not worn on user's tissue. Further, electrical energy can be spared whenever the device is not worn.

According to one option, the method can include displaying the so determined current blood oxygen saturation level on a display intended to be looked at by a user. According to one option, the method can include providing the so determined current blood oxygen saturation level to a remote entity, preferably via a wireless transmission. Results are therefore displayed directly to the user/wearer and can be forwarded to another device like a smartphone 66 either belonging to the user or to some medical staff/caretaker. Results can also be forwarded to a server 67.

Once a reliable result is obtained and displayed and/or transmitted, the process is stopped, namely steps a— to d— are halted until a next measuring sequence.

It should be understood that an accurate and reliable SPO2 result is outputted as soon as the 1D convolutional Neural Network has enough input data. Indeed, a SPO2 measuring sequence includes sampling and inputting data into the 1D convolutional Neural Network until the 1D convolutional Neural Network is full with fresh and significant data.

In practice, it can take a convergence time CT comprised between 4 seconds and 15 seconds to output an accurate and reliable SPO2 result. In one embodiment, the convergence time CT can be comprised between 8 seconds and 12 seconds.

According to one option, repeated measuring sequences are intended to perform a 'continuous' surveillance/monitoring of a user or patient. In this case, the overall method is carried out repeatedly on a user or a patient, namely steps a— to d—, once executed, are repeated after a predefined wait time comprised between 5 minutes and 30 minutes. A new measuring sequence can be delayed if the worn test function gives a negative result or if motion signals are greater than a predetermined threshold. We therefore optimize usage of electrical energy.

For patient(s) that may undergo a rather sudden respiratory trouble, monitoring the SPO2 several times per hour allows to raise an alert for a caretaker without delay if things go worse for the patient(s).

Wristwatch Example

Figure 1:
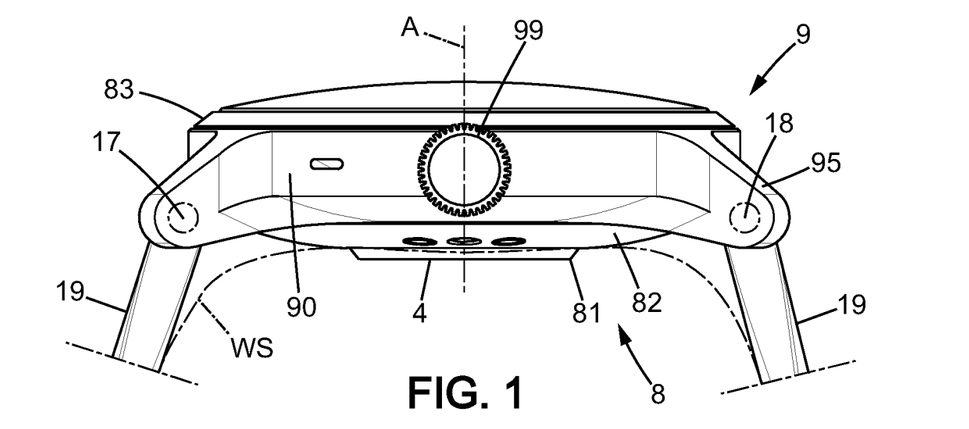
FIG. 1 is a side elevation view of an oximeter wristwatch according to the present disclosure.
Figure 2:
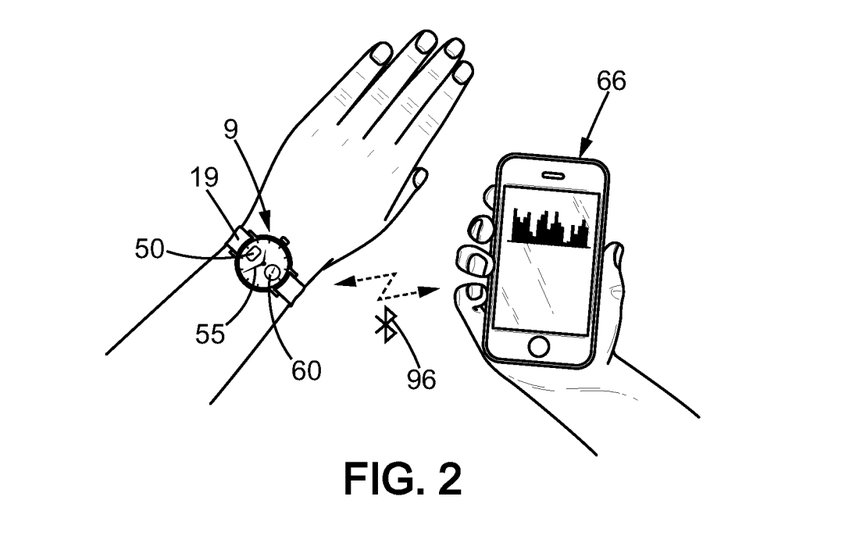
FIG. 2 illustrates such a watch worn by a user at the wrist and having a communication interface.
Figure 3:
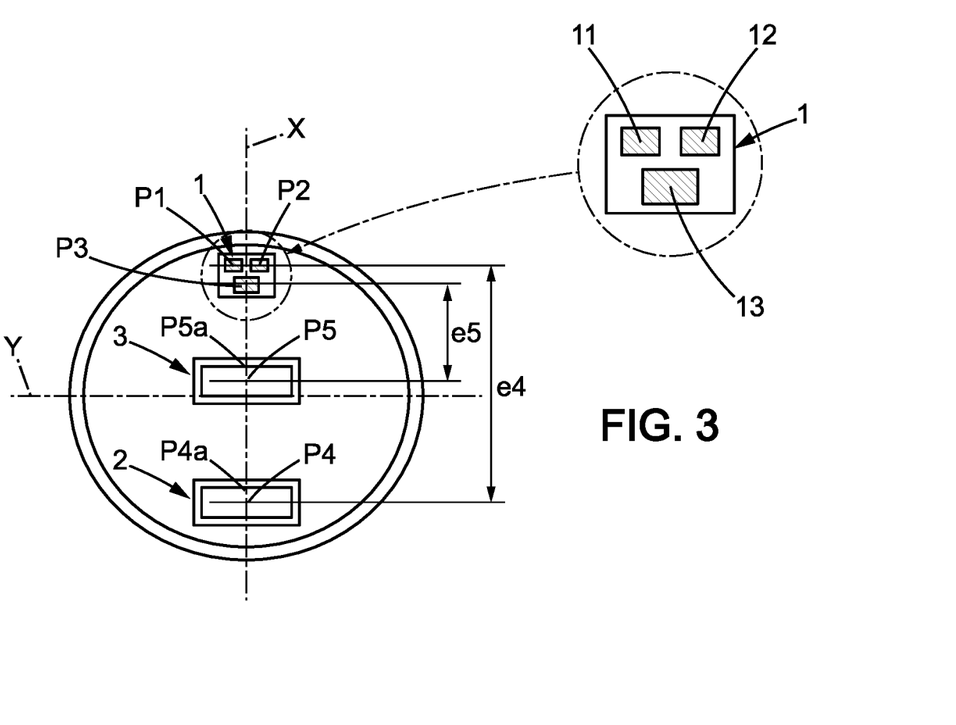
FIG. 3 shows more in details a back view of the watch centered on the glass window.

The wristband 19 is removably attached to the pairs of arms 93, 95 via two shafts 17,18 (cf FIG. 1). The abovementioned shaft allows a pivot connection of the wrist band with respect to the main casing 90.

The control unit 6 is housed in an upper area within the wristwatch. The control unit 6 is configured to handle the time display.

Figure 9:
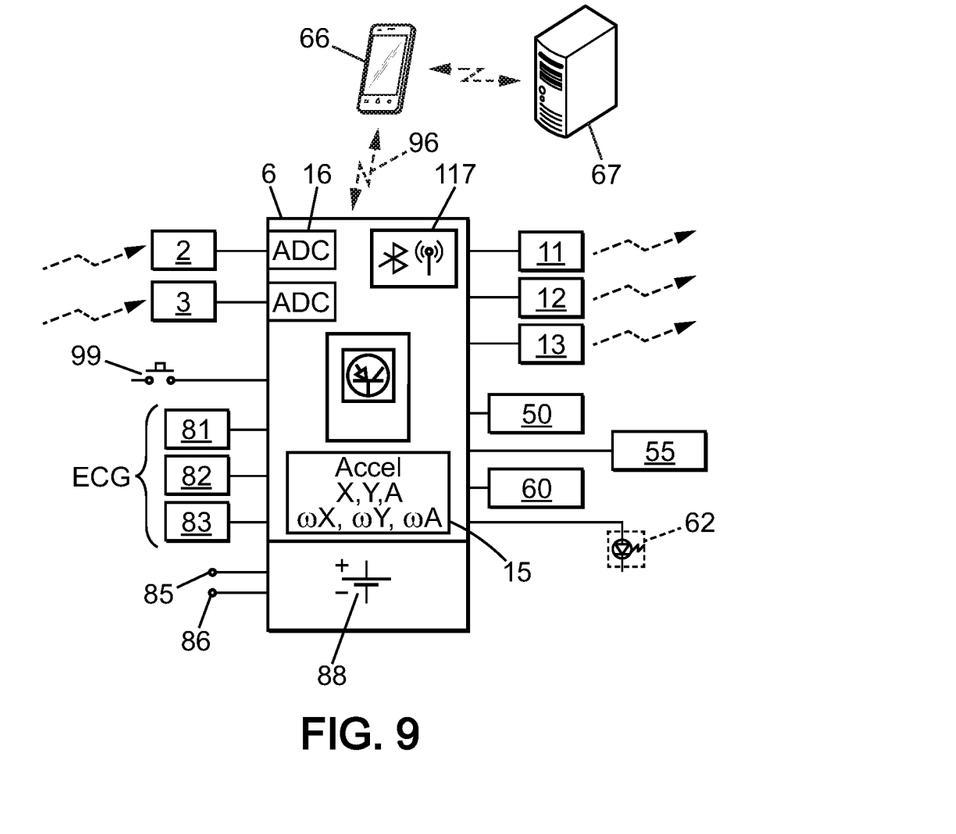
FIG. 9 shows a functional block diagram of the oximeter wristwatch of FIG. 1.

As shown at FIG. 9, the wristwatch comprises a battery 88. The battery 88 is preferably a rechargeable type battery, for which there are provided charging pins 85 86.

As known for a wristwatch, there is provided current time display at the top/front face of the watch. Here, there are provided physical hands 55, each formed as a stick pivotally mounted around axis A. However hands different from physical stick(s) can also be considered in the present scope. A completely digital solution can also be envisioned.

There is provided a control knob 99. This knob can be rotated around its axis and pushed along its axis. There is provided a front bezel ring 83, distinct from the main casing 90, the purpose of which will be seen later.

Visible from the front side of the watch, there are provided two pixelated digitally controlled area 50, 60. On said digitally controlled areas 50, 60, one displayed function is a pedometer function, other displayed data relate to or more bio-parameter(s). Some displayed functions are permanent, other are temporarily displayed.

Currently measured and/or lastly measured SpO2 (arterial blood oxygen saturation of hemoglobin) can be displayed in one of the digitally controlled area 50, 60. A result of an ECG measurement can also be temporarily displayed.

There are provided three ECG electrodes: the ring member 81, the annular cup member 82 and the front bezel ring 83.

Regarding geometric arrangement, the emission point of infrared LED 11 is at a first location denoted P1, i.e. the infrared LED 11 is arranged to emit light rays at the first position P1. The emission point of red LED 12 is at a second location denoted P2, i.e. the red LED 12 is arranged to emit light rays at the second position denoted P2. The emission point of green LED 13 is at a third location denoted P3, i.e. the green LED 13 is arranged to emit light rays at the third position denoted P3.

The broadband photodiode 2 is generally at a fourth location having a center position denoted P4. The selective photodiode 3 is generally at a fifth location having a center position denoted P5. The emission assembly 1, the broadband photodiode 2 and the selective photodiode 3 are disposed according to an in-line arrangement. Here, the selective photodiode 3 is interposed between the emission assembly 1 and the broadband photodiode 2 along the longitudinal axis X.

We note e4=Dist (P1,P4)=Dist (P2,P4). In the illustrated example (cf FIGS. 4 and 5), e4 is at least 7 mm It should be noticed that the light path for red light rays is nearly identical to the light path for infrared light rays. This enables to analyze a similar portion of the wrist tissue. Indeed P1 and P2 are spaced by a distance less that 1 mm, and red/infrared light paths go to the same target namely the broadband photodiode 2.

We note e5=Dist (P3,P5). In the illustrated example, e5 is at least 2 mm.

Performance/Results

Dataset to Develop, Calibrate and Validate this SpO2 Sensor—

A dataset was collected on healthy subjects during 5 hypoxia studies, totalling 76 subjects. It should be note that these hypoxia studies are costly and can be performed in a limited number of laboratories in the world, making the development of SpO2 sensors and algorithms quite difficult. There is no way to calibrate a SpO2 sensor on a population in normal conditions (i.e. not under induced hypoxia).

The algorithm was then validated on a separate hypoxia study which includes data from 14 subjects, and with reference data points equally distributed in the 70% to 100% range. On the validation dataset, it was found that the promoted method and device give resulting Root Mean Square Error (RMSE) less than 3.0% on both the left wrist and the right wrist, which is well below the 4.0% RMSE threshold set in the ISO 80601-2-61:2017 standard.

The invention claimed is:

1. A method to determine a current functional blood oxygen saturation level, the method comprising:
   acquiring, at a predefined sampling frequency, a photoplethysmography light response for each wavelength of a plurality of at least three wavelengths, resulting respectively in a first, second and third raw data series representing an amplitude response through a user's tissue,
   applying a low-pass filter to each of the first, second and third raw data series, resulting respectively in a first, second and third DC data series representing an unmodulated amplitude response,
   applying a high-pass filter to each of the first, second and third raw data series, or subtracting respectively first, second and third DC data series to said first, second and third raw data series, to result respectively in a first, second and third AC data series representing an unmodulated amplitude response, and
   applying a computation engine to the first, second and third AC data series, and to the first, second and third DC data series, and determining therefrom a user current blood oxygen saturation level,
   wherein the acquiring, at the predefined sampling frequency, of the photoplethysmography light response is performed by (i) a broadband photodiode configured to receive red and infrared light rays, and (ii) a selective photodiode configured to receive green light rays.

2. The method according to claim 1, wherein the computation engine comprises a one dimension convolutional Neural Network.

3. The method according to claim 2, wherein the one dimension convolutional Neural Network comprises an input layer fed only by first, second and third ratio data series.

4. The method according to claim 1, wherein the applying of the computation engine comprises:
   computing a first ratio, corresponding to the latest element of the first AC data series divided by the latest element of first DC data series, giving a first ratio data series,
   computing a second ratio, corresponding to the latest element of the second AC data series divided by the latest element of second DC data series, giving a second ratio data series,
   computing a third ratio, corresponding to the latest element of the third AC data series divided by the latest element of third DC data series, giving a third ratio data series,
   and the computation engine computes said first, second and third ratio data series.

5. The method according to claim 4, the one dimension convolutional Neural Network exhibits less than 1000 weight coefficients, and exhibits less than 1500 floating point multiplications per second.

6. The method according to claim 1, wherein the plurality of at least three wavelengths comprises:
   a first wavelength which has a center emission wavelength comprised between at 920 nm and 960 nm and emitted by an infrared LED,
   a second wavelength which has a center emission wavelength comprised between at 650 nm and 665 nm and emitted by a red LED,
   a third wavelength which has a center emission wavelength comprised between 480 nm and 540 nm and emitted by a green or blue LED.

7. The method according to claim 1, further comprising one or more of:
   displaying the so determined current blood oxygen saturation level on a display intended to be looked at by a user,
   providing the so determined current blood oxygen saturation level to a remote entity.

8. The method according to claim 7, wherein the determined current blood oxygen saturation level is provided to a remote entity via a wireless transmission.

9. The method according to claim 1, wherein the light response for each wavelength are taken at a user's wrist, and/or wherein the method is implemented in a control unit housed in a wrist-worn device.

10. The method according to claim 9, wherein the wrist-worn device is a wristwatch.

11. The method according to claim 1, carried out repeatedly on a user or a patient, wherein the acquiring, at the predefined sampling frequency, of the photoplethysmography light response, the applying of the low-pass filter, the applying of the high-pass filter and the applying of the computation engine, once executed, are repeated after a predefined wait time comprised between 5 minutes and 30 minutes.

12. The method according to claim 1, implemented in a device comprising a motion sensor, wherein whenever a motion greater than a predetermined threshold is sensed, the method further comprising a momentary suspension of displaying and outputting of the user current blood oxygen saturation level.

13. The method according to claim 1, further comprising a worn test function, wherein whenever the worn test function gives a negative result, at least displaying and outputting of the user current blood oxygen saturation level are suspended.

14. The method according to claim 13, wherein whenever the worn test function gives a negative result, the computation is suspended.

15. The method according to claim 1, wherein the predefined sampling frequency is comprised between 15 Hz and 200 Hz.

16. The method according to claim 15, wherein the predefined sampling frequency is comprised between 15 Hz and 50 Hz.

17. The method according to claim 16, wherein the predefined sampling frequency is comprised between 20 Hz and 30 Hz.

18. The method according to claim 1, wherein the applying of the low-pass filter, the applying of the high-pass filter and the applying of the computation engine are performed each time a new set of wavelength light responses is acquired.

19. A device comprising:
a plurality of LEDs, configured to emit light rays at a plurality of at least three or more wavelengths;
at least one light sensing device, and
a control unit,
the device being formed as a single unit and the control unit being configured to carry out a method to determine a current functional blood oxygen saturation level, the method including
acquiring, at a predefined sampling frequency, a photoplethysmography light response for each wavelength of the plurality of at least three wavelengths, resulting respectively in a first, second and third raw data series representing an amplitude response through a user's tissue,
applying a low-pass filter to each of the first, second and third raw data series, resulting respectively in a first, second and third DC data series representing an unmodulated amplitude response,
applying a high-pass filter to each of the first, second and third raw data series, or subtracting respectively first, second and third DC data series to said first, second and third raw data series, to result respectively in a first, second and third AC data series representing an unmodulated amplitude response, and
applying a computation engine to the first, second and third AC data series, and to the first, second and third DC data series, and determining therefrom a user current blood oxygen saturation level,
wherein the acquiring, at the predefined sampling frequency, of the photoplethysmography light response is performed by (i) a broadband photodiode configured to receive red and infrared light rays, and (ii) a selective photodiode configured to receive green light rays.

20. A device comprising:
a light emission assembly comprising an infrared LED to emit an infrared light ray with a first wavelength at a first position, a red LED to emit a red light ray with a second wavelength at a second position, and a green LED configured to emit a green light ray with a third wavelength at a third position,
a broadband photodiode configured to receive the red and infrared light rays, and a selective photodiode configured to receive the green light ray,
a control unit,
wherein the broadband photodiode is at a fourth position and the selective photodiode is at a fifth position, and
wherein a distance between the third position and the fifth position is at least 2 mm,
wherein the device is formed as a single unit and the control unit is configured to carry out a method to determine a current functional blood oxygen saturation level, the method including
acquiring, at a predefined sampling frequency, a photoplethysmography light response for each of the first, second and third wavelengths, resulting respectively in a first, second and third raw data series representing an amplitude response through a user's tissue,
applying a low-pass filter to each of the first, second and third raw data series, resulting respectively in a first, second and third DC data series representing an unmodulated amplitude response,
applying a high-pass filter to each of the first, second and third raw data series, or subtracting respectively first, second and third DC data series to said first, second and third raw data series, to result respectively in a first, second and third AC data series representing an unmodulated amplitude response, and
applying a computation engine to the first, second and third AC data series, and to the first, second and third DC data series, and determining therefrom a user current blood oxygen saturation level.

21. The device according to claim 20, wherein the device is a wristwatch.

22. The device according to claim 19, comprising a light emission assembly comprising a green LED, a red LED and an infrared LED,
wherein the infrared LED is arranged to emit light rays at a first position,
wherein the broadband photodiode is at a fourth position,
wherein a distance between the first position and the fourth position is at least 7 mm.

23. The device according to claim 19, comprising a light emission assembly comprising a green LED, a red LED and an infrared LED, wherein the light emission assembly, the broadband photodiode and the selective photodiode are disposed according to an in-line arrangement in which the selective photodiode is interposed between the light emission assembly and the broadband photodiode.

24. The device according to claim 19, wherein the device is a wristwatch.

* * * * *